US008655002B2

(12) United States Patent
Parker

(10) Patent No.: US 8,655,002 B2
(45) Date of Patent: Feb. 18, 2014

(54) PIERCING CONDUCTED BONE CONDUCTION DEVICE

(75) Inventor: John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 1175 days.

(21) Appl. No.: 12/168,620

(22) Filed: Jul. 7, 2008

(65) Prior Publication Data

US 2009/0245557 A1  Oct. 1, 2009

Related U.S. Application Data

(60) Provisional application No. 61/041,185, filed on Mar. 31, 2008.

(51) Int. Cl.
*H04R 25/00* (2006.01)

(52) U.S. Cl.
USPC ............................................. 381/326; 600/25

(58) Field of Classification Search
USPC ............................ 600/25; 381/23.1, 151, 326
See application file for complete search history.

(56) References Cited

U.S. PATENT DOCUMENTS

| 4,606,329 | A | * | 8/1986 | Hough | 600/25 |
| 4,612,915 | A | * | 9/1986 | Hough et al. | 600/25 |
| 5,430,801 | A | * | 7/1995 | Hill | 381/322 |
| 6,589,244 | B1 | * | 7/2003 | Sevrain et al. | 606/916 |
| 6,643,378 | B2 | | 11/2003 | Schumaier | |
| 6,786,860 | B2 | * | 9/2004 | Maltan et al. | 600/25 |
| 7,058,192 | B2 | * | 6/2006 | Muller et al. | 381/326 |
| 7,127,078 | B2 | * | 10/2006 | Mann et al. | 381/326 |
| 2003/0063764 | A1 | * | 4/2003 | Maltan et al. | 381/315 |
| 2006/0056649 | A1 | | 3/2006 | Schumaier | |
| 2008/0139874 | A1 | * | 6/2008 | Slattery et al. | 600/25 |
| 2008/0255406 | A1 | * | 10/2008 | Ball et al. | 600/25 |

FOREIGN PATENT DOCUMENTS

| WO | 0193645 | 12/2001 |
| WO | 2004093401 | 10/2004 |
| WO | 2005000391 | 1/2005 |

* cited by examiner

*Primary Examiner* — Steven Loke
*Assistant Examiner* — David Goodwin
(74) *Attorney, Agent, or Firm* — Kilpatrick, Townsend & Stockton, LLP.

(57) ABSTRACT

A bone conduction device for enhancing the hearing of a recipient comprising a sound input element configured to receive an acoustic sound signal; an electronics module configured generate an electrical signal representing the acoustic sound signal; a transducer configured to generate mechanical forces representing the electrical signal for delivery to the recipient's skull; one or more extensions mechanically coupled at a first portion to the transducer and further mechanically coupled at a second portion of the one or more extensions to the recipient's bone, wherein the one or more extensions are configured to transfer the mechanical forces from the transducer to the recipient's bone.

24 Claims, 9 Drawing Sheets

FIG. 3A
FIG. 3B
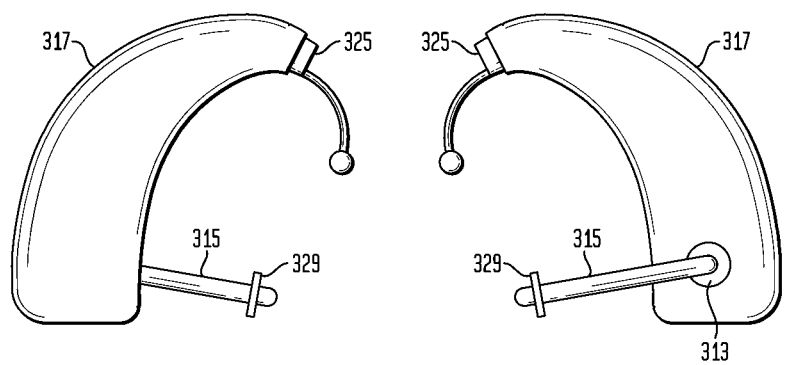
FIG. 3C
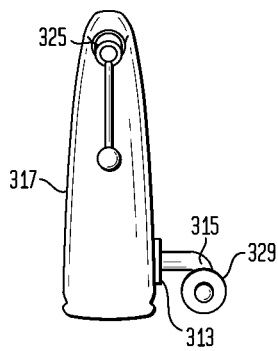

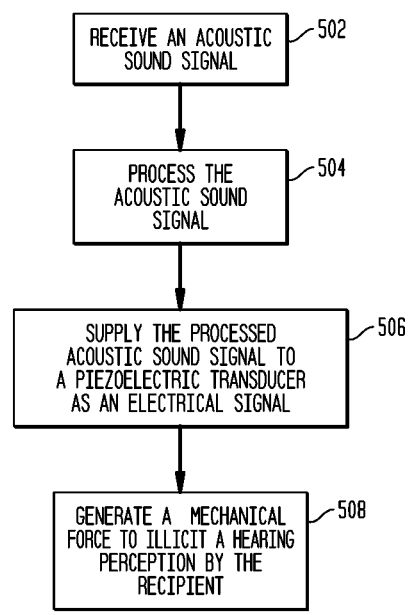

PIERCING CONDUCTED BONE CONDUCTION DEVICE

CROSS-REFERENCE TO RELATED APPLICATIONS

The present application claims the benefit of US Provisional Patent Application 61/041,185; filed Mar. 31, 2008, which is hereby incorporated by reference herein.

BACKGROUND

1. Field of the Invention

The present invention is generally directed to a bone conduction device, and more particularly, to a piercing conducted bone conduction device.

2. Related Art

Hearing loss, which may be due to many different causes, is generally of two types, conductive or sensorineural. In many people who are profoundly deaf, the reason for their deafness is sensorineural hearing loss. This type of hearing loss is due to absence, destruction, or damage to the hairs that transduce acoustic signals into nerve impulses in the cochlea. Various prosthetic hearing implants have been developed to provide individuals who suffer from sensorineural hearing loss with the ability to perceive sound. One type of prosthetic implant, referred to as a cochlear implant, uses an electrode array implanted in the cochlea. More specifically, an electrical stimulus is provided via the electrode array directly to the cochlea nerve, thereby inducing a hearing sensation in the implant recipient.

Conductive hearing loss occurs when the normal mechanical pathways, which conduct sound to hairs in the cochlea, are impeded. This problem may arise from damage to the ossicular chain to ear canal. However, individuals who suffer from conductive hearing loss frequently still have some form of residual hearing because the hairs in the cochlea are often undamaged. For this reason, individuals who suffer from conductive hearing loss are typically not candidates for a cochlear implant, because insertion of the electrode array into a cochlea results in the severe damage or destruction of the most of the hairs within the cochlea.

Sufferers of conductive hearing loss typically receive an acoustic hearing aid. Hearing aids receive ambient sound in the outer ear, amplify the sound, and direct the amplified sound into the ear canal. The amplified sound reaches the cochlea and causes motion of the cochlea fluid, thereby stimulating the hairs in the cochlea.

Unfortunately, hearing aids do not benefit all individuals who suffer from conductive hearing loss. For example, some individuals are prone to chronic inflammation or infection of the ear canal and cannot wear hearing aids. Other individuals have malformed or absent outer ear and/or ear canals as a result of a birth defect, or as a result of common medical conditions such as Treacher Collins syndrome or Microtia. Hearing aids are also typically unsuitable for individuals who suffer from single-sided deafness (i.e., total hearing loss only in one ear) or individuals who suffer from mixed hearing losses (i.e., combinations of sensorineural and conductive hearing loss). In addition to hearing aids which amplify and direct the amplified sound into the ear canal, some patients received implanted hearing aids or hearing prosthesis which have one or more components implanted in the recipient's skull or between the skull and tissue. However, some recipients are not suited for implanted hearing aids, due to the size, shape and particular condition of the recipient or their skull. In other cases, recipients are not desirous of implanted hearing aids, given their often bulky size or other factors.

Those individuals who cannot benefit from hearing aids or implanted hearing devices may benefit from hearing prostheses that are put into contact with, but not implanted or embedded within or between, the skull bone and the recipient's skin. Such hearing prostheses direct vibrations into the bone, so that the vibrations are conducted into the cochlea and result in stimulation of the hairs in the cochlea. This type of prosthesis is typically referred to as a bone conduction device.

Bone conduction devices function by converting a received sound into a mechanical vibration representative of the received sound. This vibration is then transferred to the bone structure of the skull, causing vibration of the recipient's skull and serves to stimulate the cochlea hairs, thereby inducing a hearing sensation in the recipient.

SUMMARY

According to one embodiment of the present invention, a bone conduction device for enhancing the hearing of a recipient is provided. The device comprises a sound input element configured to receive an acoustic sound signal; an electronics module configured generate an electrical signal representing the acoustic sound signal; a transducer configured to generate mechanical forces representing the electrical signal for delivery to the recipient's skull; one or more extensions mechanically coupled at a first portion to the transducer and further mechanically coupled at a second portion of the one or more extensions to the recipient's bone, wherein the one or more extensions are configured to transfer the mechanical forces from the transducer to the recipient's bone.

According to another embodiment of the present invention, a method for rehabilitating the hearing of a recipient with a bone conduction device having one or more extensions pierced through the recipient's bone, thereby mechanically coupling the one or more extensions to the recipient's bone is provided. The method comprises receiving an electrical signal representative of an acoustic sound signal; generating mechanical forces representative of the received electrical signal; and delivering the mechanical forces to the recipient's skull via the one or more pierced extensions.

According to a further embodiment of the present invention, a method for rehabilitating the hearing of a recipient with a bone conduction device configured to generate mechanical forces and having one or more extensions for mechanically coupling to the recipient's bone is provided. The method comprises piercing the recipient's bone with the one or more extensions of the bone conduction device to mechanically couple the one or more extensions to the bone; and operating the bone conduction device to generate and transfer the mechanical forces to the recipient's bone via the one or more extensions.

According to yet another embodiment of the present invention, a device configured to rehabilitate the hearing of a recipient with a bone conduction device having one or more extensions pierced through the recipient's bone, thereby mechanically coupled to the recipient's bone is provided. The device comprises means for receiving an electrical signal representative of an acoustic sound signal; means for generating mechanical forces representative of the received electrical signal; and means for delivering the mechanical forces to the recipient's skull via the one or more pierced extensions.

According to another embodiment of the present invention, a device configured to rehabilitate the hearing of a recipient with a bone conduction device configured to generate mechanical forces and having one or more extensions for mechanically coupling to the recipient's bone is provided. The device comprises means for piercing the recipient's bone to mechanically couple the one or more extensions to the bone; and means for generating and transferring the mechanical forces to the recipient's bone via the one or more extensions.

BRIEF DESCRIPTION OF THE DRAWINGS

Illustrative embodiments of the present invention are described herein with reference to the accompanying drawings, in which:

FIG. 3A is a perspective side view of a piercing conducted bone conduction device according to one embodiment of the present invention;

FIG. 3B is another perspective side view of a piercing conducted bone conduction device according to one embodiment of the present invention;

FIG. 3C is a perspective front view of a piercing conducted bone conduction device according to one embodiment of the present invention;

FIG. 5 is a flowchart illustrating the conversion of an input sound into skull vibration in a transcutaneous bone conduction device according to one embodiment of the present invention;

DETAILED DESCRIPTION

Embodiments of the present invention are generally directed to a bone conduction device for converting a received acoustic sound signal into a mechanical force delivered via a piercing secured to a recipient's bone to the recipient's hearing organs. The piercing conducted bone conduction device includes a sound input component, such as microphone, to receive the acoustic sound signal, an electronics module configured to generate an electrical signal representing the acoustic sound signal, and a transducer to convert the electrical signal into a mechanical force for delivery to the recipient's skull. In certain embodiments of the present invention, the transducer is connected to an extension arm which pierces through and remains in contact with the cartilage bone adjacent the ear canal. The force generated by the transducer is mechanically communicated to the connected piercing (extension arm), which carries that force to the cartilage bone which it pierces and is in contact with, which causes motion of the cochlea fluid and a hearing perception by the recipient.

In certain embodiments of the present invention, the transducer may comprise a piezoelectric element. The piezoelectric element converts an electrical signal applied thereto into a mechanical deformation (i.e. expansion or contraction) of the element. The amount of deformation of a piezoelectric element in response to an applied electrical signal depends on material properties of the element, orientation of the electric field with respect to the polarization direction of the element, geometry of the element, etc.

The deformation of the piezoelectric element may also be characterized by the free stroke and blocked force of the element. The free stroke of a piezoelectric element refers to the magnitude of deformation induced in the element when a given voltage is applied thereto. Blocked force refers to the force that must be applied to the piezoelectric element to stop all deformation at the given voltage. Generally speaking, piezoelectric elements have a high blocked force, but a low free stroke. In other words, when a voltage is applied to the element, the element will can output a high force, but will only a small stroke.

In some piezoelectric transducers, the maximum available transducer stroke is equivalent to the free stroke of the piezoelectric element. As such, some bone conduction devices utilizing these types of piezoelectric transducer have a limited transducer stroke and corresponding limits on the magnitude of the mechanical force that may be provided to the skull.

Figure 1A:
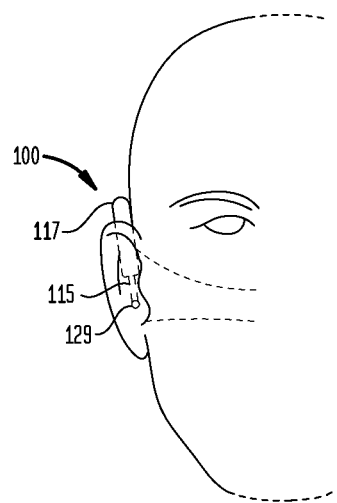
FIG. 1A is a perspective front view of a recipient with a piercing conducted bone conduction device provided according to one embodiment of the present invention.

FIG. 1A is a perspective front view of a recipient with a piercing conducted bone conduction device provided according to one embodiment of the present invention. As illustrated, the recipient is shown with piercing conducted bone conduction device 100 fitted. Device 100 is shown with sound processor/transducer 117, extension 115 and fixation stud 129, as will be described in further detail below. Extension 115 and fixation stud 129 are positioned adjacent the ear canal (shown in dashed lines) in the illustrated embodiment of the present invention. Fixation stud 129 may be visible from the front of the recipient, but extension 115 and the majority of sound processor/transducer 117 may be hidden from a third-party when the recipient is viewed from their front.

Figure 1B:
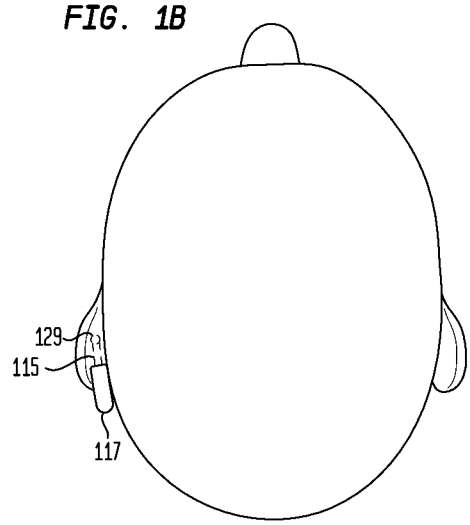
FIG. 1B is a perspective top view of a recipient with a piercing conducted bone conduction device provided according to one embodiment of the present invention.

FIG. 1B is a perspective top view of a recipient with a piercing conducted bone conduction device provided according to one embodiment of the present invention. As with FIG. 1A, the recipient is shown fitted with one embodiment of the present invention in which sound processor/transducer 117 is positioned behind the recipient's ear. Extension 115 pierces or extends through the recipient's ear, preferably through the cartilaginous portion, and is terminated with fixation stud 129.

Figure 2:
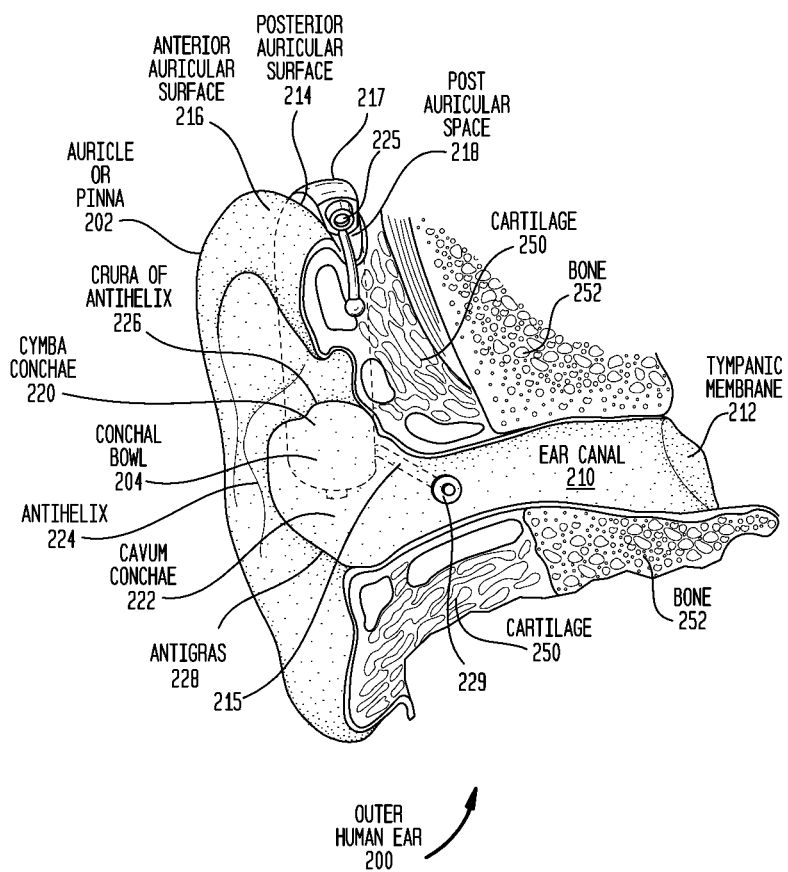
FIG. 2 is a detailed perspective view of a piercing conducted bone conduction device provided to a recipient according to one embodiment of the present invention.

FIG. 2 is a detailed perspective view of a piercing conducted bone conduction device 100, referred to in FIG. 2 as device 200, provided to a recipient according to one embodiment of the present invention. As shown, extension 215 extends from sound processor/transducer 217 through cartilage 250 of the recipient's skull and is terminated by fixation stud 229. Mechanical forces in the form of vibrations are generated by sound processor/transducer 217 and communicated to extension 215. The vibrations from extension 215 are then communicated to cartilage 250 which conducts the vibrations to the recipient's cochlea to move the fluid contained therein to generate movement of hair cells within the cochlea resulting in a hearing sensation by the recipient. As shown, sound processor/transducer 217 further comprises various other component such as microphone 225 and a retainer provided to assist in retaining the device 200 in place against the recipient's head.

Unlike other bone conducting devices, certain embodiments of the piercing conducted bone conduction device of the present invention may be fitted in place for use by the recipient without having to surgically place various device components underneath the recipient's skin, for example embedding anchors into the skull of the recipient. As recipient's cartilage 250 is relatively easy to pierce, as in the case of ear piercings, and given the limited neural and vascular systems in the cartilage surrounding the human ear, piercing the cartilage to bring a vibration transfer extension such as extension 215 into contact with the cartilage surround the recipient's ear is a relatively safe and pain-free method to implement a bone conduction device of the present invention.

The term "piercing" is to be understood to mean that extension 215 enters cartilage 250 at least partially into, and in some cases goes completely through, cartilage 250 such that extension 215 enters on one side of cartilage 250 and exits out another side of cartilage 250. It is not a requirement of the present invention that extension 215 extend completely through cartilage 250; only that extension 215 at least partially enters or is otherwise firmly attached to cartilage 250 such that vibration and other mechanical forces exerted on extension 250 is substantially efficiently communicated down extension 215 to cartilage 250. Furthermore, it is to be understood that various components of the present invention may be implanted underneath the recipient's skin, including embedding one or more components within the recipient's skull.

Furthermore, while various embodiments of the present invention are described herein as having a single extension 215, it is to be understood that other embodiments of the present invention may also incorporate multiple extensions which are each attached to the recipient's bone.

FIGS. 3A-3C are perspective side, other side, and front views respectively of a piercing conducted bone conduction device according to one embodiment of the present invention. As shown, sound processor/transducer 317 is attached to extension 315 by coupler 313. Fixation stud 329 and microphone 325, as described above in conjunction with FIG. 2, are also illustrated.

Figure 4A:
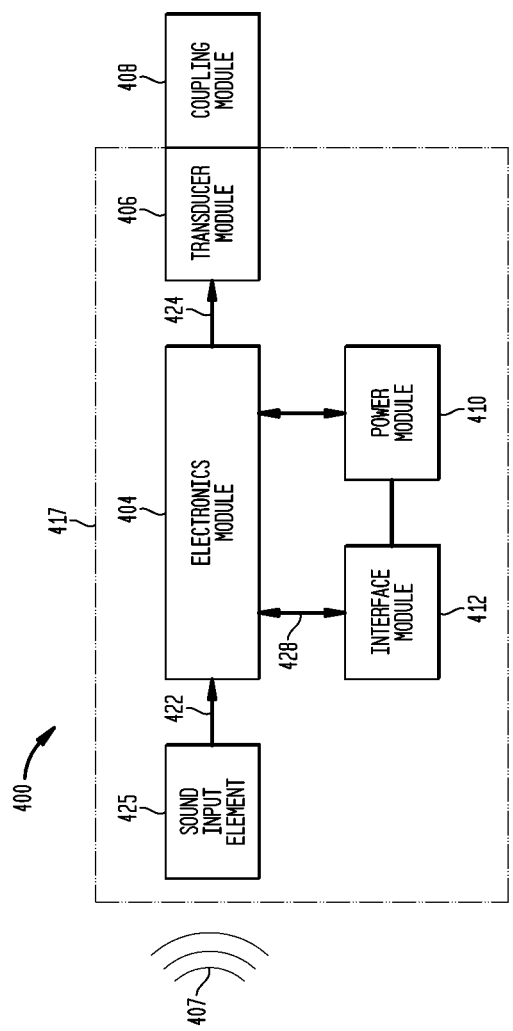
FIG. 4A is a high-level functional block diagram of a piercing conducted bone conduction device according to one embodiment of the present invention, such as the device of FIG. 1A.

FIG. 4A is a high-level functional block diagram of a piercing conducted bone conduction device according to one embodiment of the present invention, such as the device of FIG. 1A.

A functional block diagram of one embodiment of piercing conducted bone conduction device 100, referred to as piercing conducted bone conduction device 400, is shown in FIG. 4A. In the illustrated embodiment, a sound 207 is received by a sound input element 425. In some embodiments, sound input element 425 is a microphone configured to receive sound 207, and to convert sound 207 into an electrical signal 422. As described below, in other embodiments sound 207 may received by sound input element 425 as an electrical signal.

As shown in FIG. 4A, electrical signal 422 is output by sound input element 425 to an electronics module 404. Electronics module 404 is configured to convert electrical signal 422 into an adjusted electrical signal 424. As described below in more detail, electronics module 404 may include a sound processor, control electronics, transducer drive components, and a variety of other elements.

As shown in FIG. 4A, transducer 406 receives adjusted electrical signal 424 and generates a mechanical output force that is delivered to the skull of the recipient via extension 115, shown in FIG. 4A as coupling module 408, that is coupled to piercing conducted bone conduction device 400. Delivery of this output force causes one or more of motion or vibration of the recipient's skull, thereby activating the hair cells in the cochlea via cochlea fluid motion.

FIG. 4A also illustrates a power module 410. Power module 410 provides electrical power to one or more components of bone conduction device 400. For ease of illustration, power module 410 has been shown connected only to interface module 412 and electronics module 404. However, it should be appreciated that power module 410 may be used to supply power to any electrically powered circuits/components of piercing conducted bone conduction device 400.

Bone conduction device 400 further includes an interface module 412 that allows the recipient to interact with device 400. For example, interface module 412 may allow the recipient to adjust the volume, alter the speech processing strategies, power on/off the device, etc. Interface module 412 communicates with electronics module 404 via signal line 428.

In the embodiment illustrated in FIG. 4A, sound pickup device 425, electronics module 404, transducer 406, power module 410 and interface module 412 have all been shown as integrated in a single housing, referred to as housing 417. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

In embodiments of the present invention, transducer 406 may be one of many types and configurations of transducers, now known or later developed. In one embodiment of the present invention, transducer 406 may comprise a piezoelectric element which is configured to deform in response to the application of electrical signal 424. Piezoelectric elements that may be used in embodiments of the present invention may comprise, for example, piezoelectric crystals, piezoelectric ceramics, or some other material exhibiting a deformation in response to an applied electrical signal. Exemplary piezoelectric crystals include quartz ($SiO_2$), Berlinite ($AlPO_4$), Gallium orthophosphate ($GaPO_4$) and Tourmaline. Exemplary piezoelectric ceramics include barium titanate (BaTiO30), lead zirconate titanate (PZT), or zirconium (Zr).

Some piezoelectric materials, such as barium titanate and PZT, are polarized materials. When an electric field is applied across these materials, the polarized molecules align themselves with the electric field, resulting in induced dipoles within the molecular or crystal structure of the material. This alignment of molecules causes the deformation of the material.

In other embodiments of the present invention, other types of transducers may be used. For example, various motors configured to operate in response to electrical signal 424 may be used.

In the embodiment illustrated in FIG. 4A, coupling module comprising an extension arm, as described further below, is configured to be attached to housing 417. In the embodiment shown in FIG. 4A, transducer 406 is also configured to be attached to housing 417. As such, in this embodiment, vibration from transducer 406 is provided to coupling module 408 through housing 417.

In certain embodiments of the present invention, electronics module 404 includes a printed circuit board (PCB) to electrically connect and mechanically support the components of electronics module 404. Sound input element 425 may comprise one or more microphones (not shown) and is attached to the PCB.

Figure 4B:
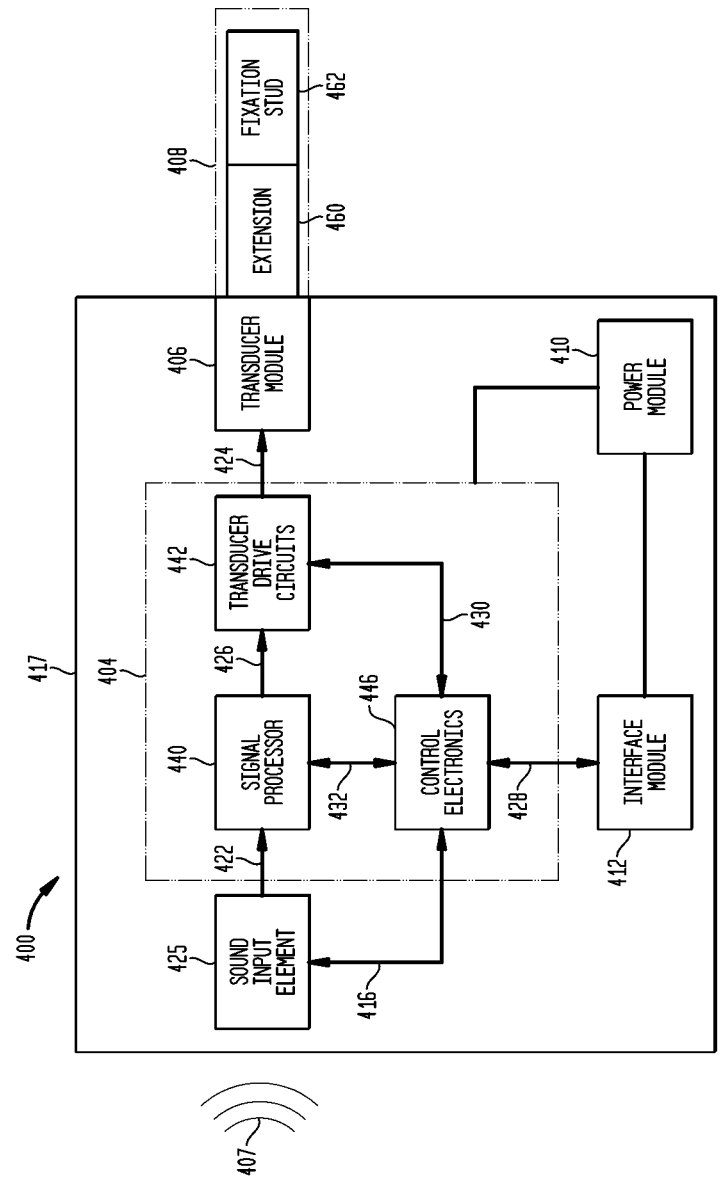
FIG. 4B is a detailed functional block diagram of the piercing conducted bone conduction device illustrated in FIG. 4A.

FIG. 4B provides a more detailed view of bone conduction device 400 of FIG. 4A. In the illustrated embodiment, electronics module 404 comprises a sound processor 440, transducer drive components 442 and control electronics 446. As explained above, in certain embodiments sound input element 425 comprises a microphone configured to convert a received acoustic signal into electrical signal 422. In other embodiments, as detailed below, sound input element 425 receives sound 207 as an electrical signal.

In embodiments of the present invention, electrical signal 422 is output from sound input element 425 to sound processor 440. Sound processor 440 uses one or more of a plurality of techniques to selectively process, amplify and/or filter electrical signal 422 to generate a processed signal 424A. In certain embodiments, sound processor 440 may comprise substantially the same sound processor as is used in an air conduction hearing aid. In further embodiments, sound processor 440 comprises a digital signal processor.

Processed signal 424A is provided to transducer drive components 442. Transducer drive components 442 output a drive signal 424B, to transducer 406. Based on drive signal 424B, transducer 406 provides the output force to the skull of the recipient through extension 460 of coupling module 408.

For ease of description the electrical signal supplied by transducer drive components 442 to transducer 406 has been referred to as drive signal 424B. However, it should be appreciated that processed signal 424B may comprise an unmodified version of processed signal 424A.

As noted above, transducer 406 generates an output force to the skull of the recipient via coupling module 408. As shown in FIG. 4B, in one embodiment of the present invention, coupling module 408 comprises extension 460 and fixation stud 462. Fixation stud 462 is configured to couple to extension 460 from the other side of recipient's bone, for example cartilage 250, such that housing 417 and fixation stud 462 are on either side of the recipient's bone to which extension 460 is mechanically coupled. In different embodiments of the present invention, fixation stud 462 may be one of various types or designs or fixation mechanisms. For example, fixation stud 462 may comprise a snap component which attaches to a corresponding snap component on the end of extension 460. Alternatively, fixation stud 462 may comprise screw threads which fit corresponding threading provided within the end of extension 460. It will be obvious to persons having skill in the art that other mechanisms provided on fixation stud 462 and/or at the end of extension 460 may be used as part of one embodiment of the present invention.

As noted previously, extension 460 is mechanically coupled to the recipient's bone, for example to cartilage 250. Extension 460 may further be coupled to transducer 406 or housing 417. In certain embodiments of the present invention, extension 460 is attached to transducer 406 and vibration is received directly therefrom. In other embodiments, extension 460 is attached to housing 417 and vibration is applied from transducer 406 to housing 417, which in turns transfers that force to extension 460. According to one embodiment of the present invention in which coupling 140 comprises extension 460, the vibration received by extension 460 from transducer 406 causes extension 460 to vibrate. The vibration, communicated from extension 460 to transducer module 460 is then transferred from extension 460 to the recipient's bone 250.

As noted above, a recipient may control various functions of the device via interface module 412. Interface module 412 includes one or more components that allow the recipient to provide inputs to, or receive information from, elements of bone conduction device 400.

As shown, control electronics 446 may be connected to one or more of interface modules 412, sound pickup device 425, sound processor 440 and/or transducer drive components 442. In embodiments of the present invention, based on inputs received at interface module 412, control electronics 446 may provide instructions to, or request information from, other components of bone conduction device 400. In certain embodiments, in the absence of user inputs, control electronics 446 control the operation of bone conduction device 400.

FIG. 5 illustrates the conversion of an input acoustic sound signal into a mechanical force for delivery to the recipient's skull in accordance with embodiments of piercing conducted bone conduction device 400. At block 502, piercing conducted bone conduction device 400 receives an acoustic sound signal. In certain embodiments, the acoustic sound signal is received via microphones. In other embodiments, the input sound is received via an electrical input. In still other embodiments, a telecoil integrated in, or connected to, piercing conducted bone conduction device 400 may be used to receive the acoustic sound signal.

At block 504, the acoustic sound signal received by piercing conducted bone conduction device 400 is processed by the speech processor in electronics module 404. As explained above, the speech processor may be similar to speech processors used in acoustic hearing aids. In such embodiments, speech processor may selectively amplify, filter and/or modify acoustic sound signal. For example, speech processor may be used to eliminate background or other unwanted noise signals received by piercing conducted bone conduction device 400.

At block 506, the processed sound signal is provided to transducer 406 as an electrical signal. At block 508, transducer 406 converts the electrical signal into a mechanical force configured to be delivered to the recipient's skull via coupling module 408 so as to illicit a hearing perception of the acoustic sound signal.

Figure 6A:
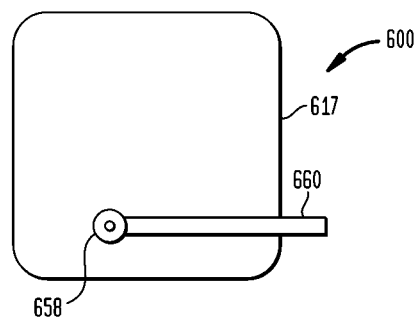
FIG. 6A is a perspective side view of a piercing conducted bone conduction device according to one embodiment of the present invention.
Figure 6B:
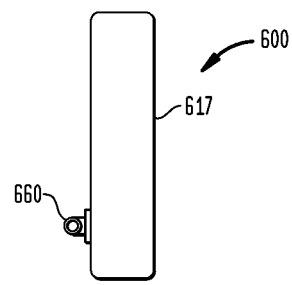
FIG. 6B is a perspective front view of the piercing conducted bone conduction device according to the embodiment illustrated in FIG. 6A.
Figure 7A:
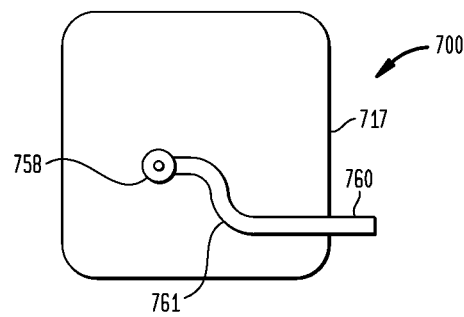
FIG. 7A is a perspective side view of a piercing conducted bone conduction device according to one embodiment of the present invention.
Figure 7B:
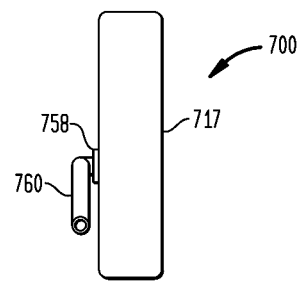
FIG. 7B is a perspective front view of the piercing conducted bone conduction device according to the embodiment illustrated in FIG. 7A.

FIGS. 6A-6B are perspective side and front views of piercing conducted bone conduction device 100, referred to in FIGS. 6A-6B as device 600, according to one embodiment of the present invention. As illustrated, device 600 comprises housing 617, coupler 658 and extension 660 attached to coupler 658. In the embodiment illustrated in FIGS. 6A-6B, extension 660 is substantially straight. For the sake of simplicity, housing 617 is shown as having a rectangular configuration. However, it is to be understood that housing 617 may be shaped in any number of ways, depending on where on the recipient's body it is to be positioned and worn, in addition to depending on the components contained therein, for example, sound processor (not shown), transducer (not shown), power module (not shown), among others. Coupler 658 is illustrated in FIGS. 6A-6B as a simple connection mechanism between extension 660 and housing 617. FIGS. 7A-7B are perspective side and front views of piercing conducted bone conduction device 100, referred to in FIGS. 7A-7B as device 700, according to another embodiment of the present invention. Device 700 illustrated in FIGS. 7A-7B comprise the various components described in conjunction with FIGS. 6A-6B, but in this particular embodiment of the present invention, extension 760 comprises a bend 761. Bend 761 permits alternative designs for device 700 in which coupler 758 may necessarily be positioned in a location on housing 717 at which a straight extension component may not be able to connect to the recipient's bone or be in an optimal operating position. Although a simple bend 761 is illustrated in FIGS. 7A-7B, it is to be understood that variations of bend 761, including complex or multi-part bends may be incorporated in other embodiments of the present invention.

Figure 8A:
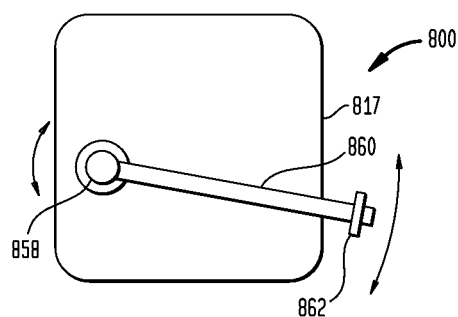
FIG. 8A is a perspective side view of a piercing conducted bone conduction device according to one embodiment of the present invention.
Figure 8B:
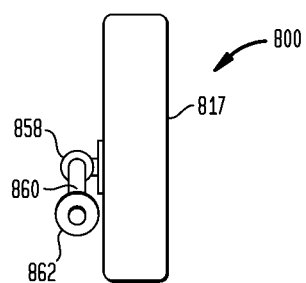
FIG. 8B is a perspective front view of the piercing conducted bone conduction device according to the embodiment illustrated in FIG. 8A.

FIGS. 8A-8B are perspective side and front views of piercing conducted bone conduction device 100, referred to in FIGS. 8A-8B as device 800, according to another embodiment of the present invention. Device 800 comprises components similar to those described in conjunction with FIGS. 6A-6B. In addition, device 800 further illustrates an embodiment having fixation stud 862 and a rotatable coupler 858. Rotatable coupler 858 may comprise a rotating hinge, joint, or other mechanism which allows extension 860 to rotate with respect to housing 817. The ability of extension 860 to rotate permits it to accommodate movements by the recipient which may exert different amounts of force on extension 860 versus housing 817. By rotating, those different forces may be absorbed without causing housing 817 or extension 860 from becoming separated from the recipient's body in an undesirable manner.

Figure 9A:
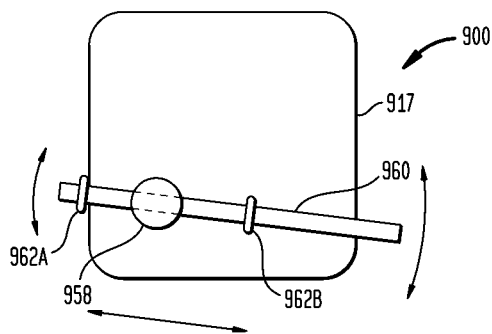
FIG. 9A is a perspective side view of a piercing conducted bone conduction device according to one embodiment of the present invention.
Figure 9B:
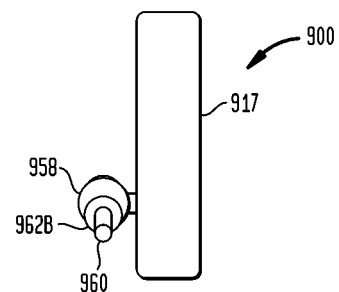
FIG. 9B is a perspective front view of the piercing conducted bone conduction device according to the embodiment illustrated in FIG. 9A.

FIGS. 9A-9B are perspective side and front views of piercing conducted bone conduction device 100, referred to in FIGS. 9A-9B as device 900, according to another embodiment of the present invention. Device 900 comprises components similar to those described in conjunction with FIGS. 6A-6B. In addition, the particular embodiment illustrated as device 900 further comprises translatable extension 960 and stoppers 962A and 962B (collectively referred to as stoppers 962). Coupler 958 is configured similarly to coupler 858 described above in conjunction with FIGS. 8A-8B, but is further configured to permit extension 960 to slide or translate through coupler 958, such that extension 960 is capable of both rotating about coupler 958 with respect to housing 917 as well as translate through coupler 958. The ability of extension 960 to both rotate and translate allows it to absorb even more differential force exerted by the recipient on extension 960 and other components of the present invention, for example housing 917. Stoppers 962 disposed at opposite ends of extension 960 with respect to coupler 958 are securely coupled to extension 960 and are configured to limit the extent to which extension 960 may translate, so that they do not translate beyond a certain length. Although stoppers 962 are illustrated as being washer-like, it is to be understood that stoppers 962 may take any other form, and may be configured solely to provide the translation limiting function or to provide that and other functions concurrently.

Figure 10A:
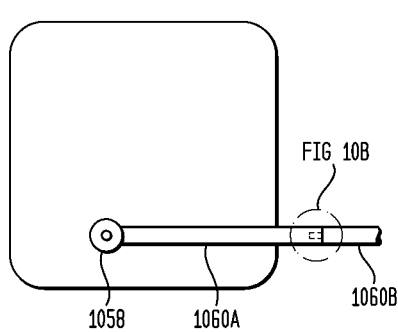
FIG. 10A is a perspective side view of a piercing conducted bone conduction device according to one embodiment of the present invention.
Figure 10B:
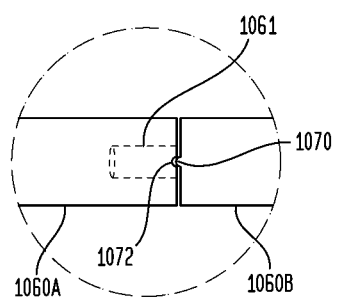
FIG. 10B is a partial perspective view of the piercing conducted bone conduction device according to the embodiment illustrated in FIG. 10A.
Figure 10C:
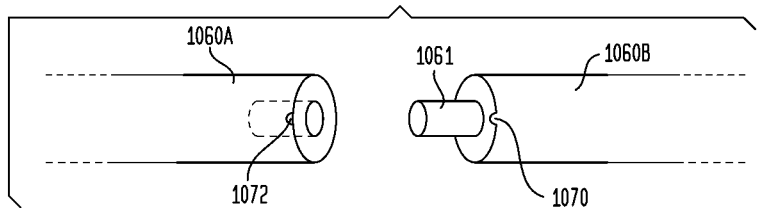
FIG. 10C is another partial perspective view of the piercing conducted bone conduction device according to the embodiment illustrated in FIG. 10A.

FIGS. 10A-10C are perspective side and close-up views of piercing conducted bone conduction device 100, referred to in FIGS. 10A-10C as device 1000, according to another embodiment of the present invention. Device 1000 comprises components similar to those described above in conjunction with FIGS. 6A-6B. In the embodiment illustrated in FIGS. 10A-10C, extension components 1060A and 1060B are two separate components which are joined together into extension 1060 prior to operation of device 1000. FIG. 10B illustrates a close-up view of the connection point between extension component 1060A and 1060B in which a female receptacle 1059 and a male projection 1061 are in a joined configuration. Additionally, insert 1070 and groove 1072 are illustrated in an interlocking configuration. In the illustrated embodiment, female receptacle 1059 and male projection 1061 cooperate to provide an anti-bending feature to the combined extension components 1060A and 1060B. Furthermore, in the illustrated embodiment of the present invention, insert 1070 and groove 1072 cooperate to provide an anti-rotation benefits to the joined extension components 1060A and 1060B. It is to be understood that the anti-bending and anti-rotation features described above are only exemplary embodiments of such mechanisms and other mechanisms may be incorporated into embodiments of the present invention to provide the described and other benefits.

By having extension 1060 comprise separate components 1060A and 1060B, it is possible for the recipient to fix extension component 1060B using a fixation stud (not shown) to the recipient's bone as described above. When the recipient is desirous of quickly detaching housing 1017 from their body, the recipient can operate components 1059, 1061, 1070, 1072 or other similar components to separate housing 1017 with extension component 1060A still attached thereto from extension component 1060B which remains attached to the recipient's bone. This may be particularly useful where fixation stud (not shown) is a screw-type as described above which may take significant time and manual dexterity to loosen.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:
1. A device for evoking a hearing percept of a recipient, comprising:
   a sound input element configured to receive an acoustic sound signal;
   an electronics module configured generate an electrical signal representing said acoustic sound signal;
   a transducer configured to generate mechanical forces representing said electrical signal;
   one or more extensions mechanically coupled at a first portion to said transducer and configured to be mechanically coupled at a second portion of said one or more extensions to cartilage of the recipient such that said one or more extensions transfer said mechanical forces from said transducer to the recipient's cartilage so as to vibrate the cartilage.

2. The device of claim 1, wherein said one or more extensions are configured to mechanically couple to the recipient's cartilage adjacent an ear canal of the recipient.

3. The device of claim 1, wherein said transducer comprises a piezoelectric element.

4. The device of claim 1, wherein said one or more extensions are configured to rotate with respect to said transducer.

5. The device of claim 1, wherein said one or more extensions are configured to translate with respect to said transducer.

6. The device of claim 5, wherein said one or more extensions are further configured to rotate with respect to said transducer.

7. The device of claim 1, wherein said one or more extensions comprise one or more bends.

8. The device of claim 1, wherein said one or more extensions comprise two or more extension components configured to be joined together.

9. The device of claim 1, further comprising:
one or more fixation studs each configured to be coupled to one end of said one or more extensions extending through the recipient's cartilage.

10. The device of claim 9, wherein said one or more fixation studs comprises snap lock mechanisms each configured to couple to said one or more extensions.

11. A method for evoking a hearing percept of a recipient with a vibratory device having one or more extensions pierced through the recipient's cartilage extending from a position external to the recipient to an outer ear canal of the recipient, thereby mechanically coupling the one or more extensions to at least one of the recipient's outer ear canal or tissue of the recipient proximate thereto, comprising:
receiving an electrical signal representative of an acoustic sound signal;
generating, externally to the recipient, mechanical forces representative of the received electrical signal; and
delivering said mechanical forces to the outer ear canal via the one or more pierced extensions so as to vibrate the said outer ear canal or tissue of the recipient.

12. A method for evoking a hearing percept of a recipient with a vibratory device configured to generate mechanical forces and having one or more extensions for mechanically coupling to cartilage of the recipient, comprising:
mechanically coupling a vibratory component of the vibratory device to the cartilage via the one or more extensions; and
operating the vibratory device to generate and transfer the mechanical forces to the recipient's cartilage via the one or more extensions so as to vibrate the recipient's cartilage.

13. The method of claim 12, wherein said one or more extensions extends only partially into the recipient's cartilage.

14. The method of claim 12, wherein said one or more extensions comprise two or more extension components, further comprising:
joining the two or more extension components to form a mechanically stable extension.

15. A device configured to evoke a hearing percept of a recipient with a vibratory device having one or more extensions pierced through the recipient extending from a position external to the recipient to at least proximate an outer ear canal of the recipient, thereby mechanically coupled to the recipient's outer ear canal, comprising:
means for receiving an electrical signal representative of an acoustic sound signal;
means for generating, externally to the recipient, mechanical forces representative of the received electrical signal; and
means for delivering said mechanical forces to the recipient's outer ear canal so as to vibrate the said outer ear canal of the recipient.

16. The device of claim 15, wherein said means for delivering said mechanical forces to the recipient's outer ear canal comprises one or more extensions configured to mechanically couple to cartilage of the recipient adjacent the outer ear canal.

17. The device of claim 15, wherein said means for generating mechanical forces comprises a piezoelectric element.

18. The device of claim 15, wherein said means for delivering said mechanical forces to the recipient's outer ear canal are configured to rotate with respect to a vibratory transducer of the vibratory device.

19. The device of claim 15, wherein said means for delivering said mechanical forces to the recipient's outer ear canal are configured to translate with respect to a vibratory transducer of the vibratory device.

20. The device of claim 19, wherein said means for delivering said mechanical forces to the recipient's outer ear canal are further configured to rotate with respect to said transducer.

21. The device of claim 15, wherein said means for delivering said mechanical forces to the recipient's outer ear canal comprise two or more extension components configured to be joined together.

22. A device, comprising:
a behind the ear (BTE) device including:
a sound input element configured to receive an acoustic sound signal; and
a transducer configured to generate vibrations representing said received acoustic sound signal; and
a vibration conductor extending away from the BTE device and configured to transfer the generated vibrations from the BTE device to cartilage of the recipient to vibrate the cartilage of the recipient and to evoke a hearing percept.

23. The device of claim 22, wherein:
the vibration conductor is configured to couple to bone of the recipient to transfer the generated vibrations to the bone to evoke the hearing percept.

24. The device of claim 22, wherein:
the vibration conductor is configured to couple to cartilage of the recipient to transfer the generated vibrations to the cartilage to evoke the hearing percept.

* * * * *